US012109716B2

(12) United States Patent
Du et al.

(10) Patent No.: US 12,109,716 B2
(45) Date of Patent: Oct. 8, 2024

(54) SYSTEMS AND METHODS FOR PROVIDING MEDICATION VIA ROBOTIC ARM

(71) Applicant: Advanced Robotics Corp., Pasadena, CA (US)

(72) Inventors: Yuliang Du, San Gabriel, CA (US); Kang-Hao Peng, Pasadena, CA (US); Flavio Ornelas, Sylmar, CA (US); Ken Chen, Pasadena, CA (US)

(73) Assignee: Advanced Robotics Corp., Pasadena, CA (US)

( * ) Notice: Subject to any disclaimer, the term of this patent is extended or adjusted under 35 U.S.C. 154(b) by 534 days.

(21) Appl. No.: 17/381,085

(22) Filed: Jul. 20, 2021

(65) Prior Publication Data
US 2022/0250249 A1    Aug. 11, 2022

Related U.S. Application Data

(60) Provisional application No. 63/148,003, filed on Feb. 10, 2021.

(51) Int. Cl.
*B25J 9/16* (2006.01)
*A61B 34/00* (2016.01)
*A61B 34/30* (2016.01)
*B25J 13/00* (2006.01)
*G16H 10/60* (2018.01)

(52) U.S. Cl.
CPC ............. *B25J 9/1697* (2013.01); *A61B 34/30* (2016.02); *A61B 34/70* (2016.02); *B25J 13/003* (2013.01); *G16H 10/60* (2018.01)

(58) Field of Classification Search
CPC . B25J 13/003; B25J 19/023; B25J 5/04; B25J 9/0018; B25J 9/1615; B25J 9/1697; G07F 17/0092; G16H 10/60; G16H 20/13; G16H 40/20
See application file for complete search history.

(56) References Cited

U.S. PATENT DOCUMENTS

| 6,711,460 | B1 * | 3/2004 | Reese | G16H 20/10 700/216 |
| 8,060,248 | B1 * | 11/2011 | Boyer | B65B 57/20 700/235 |
| 11,066,240 | B1 * | 7/2021 | Maxwell | G07F 17/12 |
| 11,820,543 | B1 * | 11/2023 | Hoffman | G05B 15/02 |
| 11,842,316 | B1 * | 12/2023 | Hoffman | G06Q 10/0832 |

(Continued)

*Primary Examiner* — Jaime Figueroa
*Assistant Examiner* — Zachary Joseph Wallace
(74) *Attorney, Agent, or Firm* — Foley & Lardner LLP

(57) ABSTRACT

A system for providing medication to a customer includes a movable structure with a robotic arm including one or more joints, actuators, and segments, each of which is structured to move a robotic manipulator coupled to an end of the robotic arm. The robotic manipulator is configured to retrieve and release a container containing the medication. The robotic arm further includes a camera and microphone, as well as a computing system that includes at least one processor coupled to a memory storing instructions. When executed by the at least one processor, the memory causes the computing system to capture identifying data regarding a customer; identify the customer based on the identifying data; associate the customer with a medication order; and retrieve.

20 Claims, 10 Drawing Sheets

(56) References Cited

U.S. PATENT DOCUMENTS

| | | | |
|---|---|---|---|
| 2015/0302177 A1* | 10/2015 | Parviainen | G16H 20/13 |
| | | | 700/236 |
| 2018/0082757 A1* | 3/2018 | Chambers | G07F 11/165 |
| 2018/0233220 A1* | 8/2018 | Trent | G16H 20/13 |
| 2019/0102965 A1* | 4/2019 | Greyshock | G07F 17/0092 |
| 2021/0150846 A1* | 5/2021 | Parviainen | G07F 11/42 |

* cited by examiner

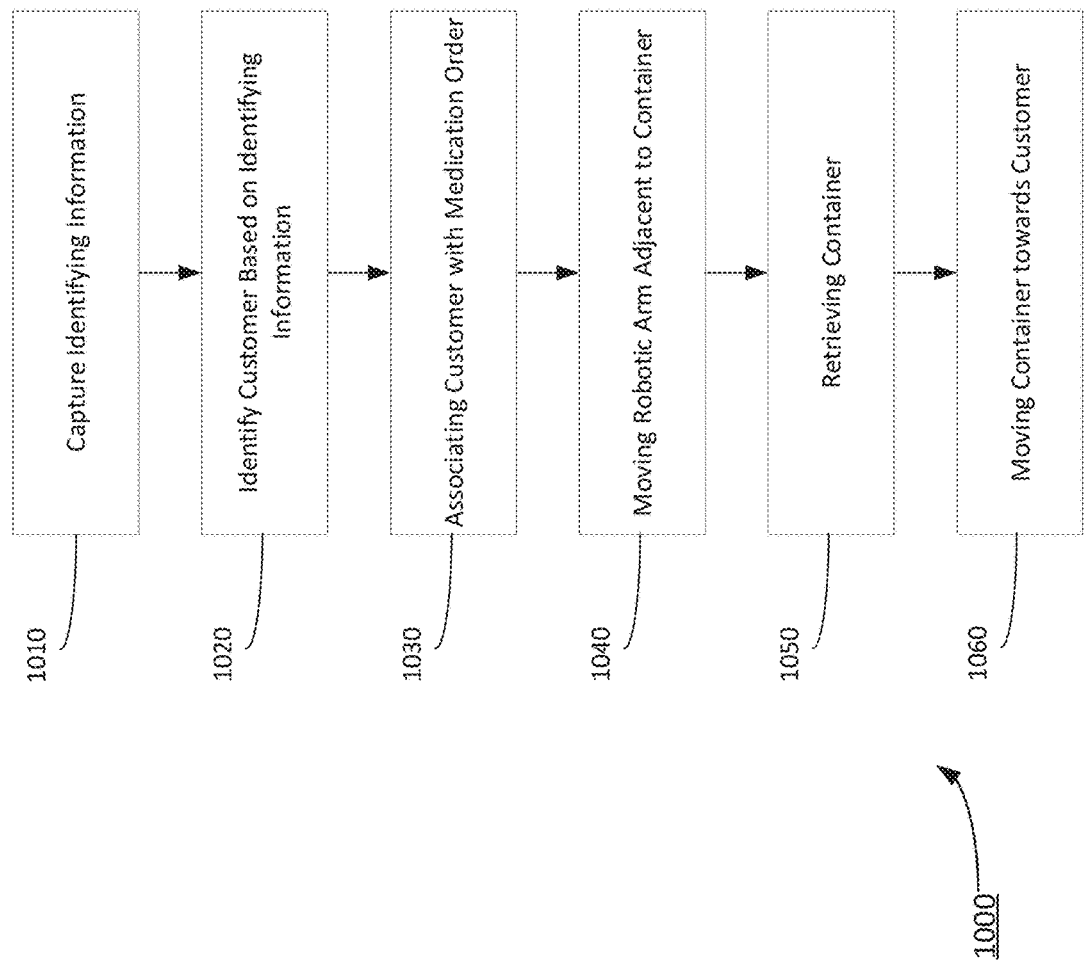

SYSTEMS AND METHODS FOR PROVIDING MEDICATION VIA ROBOTIC ARM

CROSS-REFERENCE

The present application claims the benefit of and priority to U.S. Pat. App. No. 63/148,003 entitled "DEVICE TO RELIABLY DELIVER OBJECTS IN A CONFINED AREA," filed Feb. 10, 2021, the contents of which are incorporated herein in their entirety and for all purposes.

TECHNICAL FIELD

The present disclosure relates to a robotic arm. Specifically, the present disclosure relates to a robotic arm including a computer that performs the services of a pharmacy through communication with a cloud-based backend system.

BACKGROUND

A traditional pharmacy requires a great amount of human activity in order to maintain and track inventory, dispense medication, and provide counseling to and interact with consumers. Even in those pharmacies that do feature robotics in some capacity, the robotics lack direct customer service and are generally limited to distributing medications from a medication cabinet and moving to adjacent staging area, similar to a vending machine. Especially in light of the global pandemic that has revealed the importance of contactless medicine, reducing the amount of human interaction for pharmacy pickups would provide additional utility. Furthermore, pharmacy customers are often forced to wait in long lines to pick up their medications, as inefficiencies in the pickup process can quickly build up due to the large volume of customers that require pharmacy services.

SUMMARY

One embodiment relates to a system for providing medication to a customer. The system includes a movable structure that includes a robotic arm comprising one or more joints, one or more actuators, and one or more segments, each of which is structured to move a robotic manipulator coupled to an end of the robotic arm. The robotic manipulator is configured to retrieve and release an object, (e.g., a container containing the medication, a delivery bag, etc.). The movable structure further includes at least one of a camera or a microphone; and a computing system comprising at least one processor coupled to a memory storing instructions that, when executed by the at least one processor, causes the computing system to perform operations comprising: capturing identifying data regarding a customer; identifying the customer based on the identifying data; associating the customer with a medication order; and retrieving the medication from the medication order by: moving the robotic arm adjacent to the object containing the medication based on predetermined mapping; retrieving the object using the robotic manipulator based on at least one image or at least one video captured by the camera; and moving the object toward the customer by moving the robotic arm.

Another embodiment relates to a method for providing medication to a customer. The method includes capturing identifying data regarding a customer; identifying the customer based on the identifying data; associating the customer with a medication order; and retrieving the medication from the medication order by: moving a robotic arm adjacent to an object containing the medication based on predetermined mapping; retrieving the object using a robotic manipulator of the robotic arm based on at least one image or at least one video captured by a camera of the robotic arm; and moving the object toward the customer by moving the robotic arm.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE FIGURES

FIG. 10 is a flowchart of a method for servicing a customer at a pharmacy, according to some arrangements.

DETAILED DESCRIPTION

Implementations relate to apparatus, systems, and methods for a robotic arm coupled with a computer for automated operation of a pharmacy. Particular implementations relate to a robotic arm that includes a manipulator or jaw on the end of the robotic arm and may be mounted on a rail system to facilitate movement of the arm about a room. A computer is coupled to or disposed within the robotic arm and controls movement of the robotic arm. Cameras, microphones, and/or speakers are included with the robotic arm and communicate with the computer to provide a complete picture of the robotic arm's surroundings. The computer is also in communication with a cloud that stores data related to patient care and to medication information. Because consumers rely on pharmacists for counseling and instructions, it would be further beneficial for a robotic system that replaces human pharmacists to similarly be able to provide counseling and instruction. If a robotic system is able to replace the basic functionality otherwise provided by humans, the robotic system would be able to do the same actions with an increased efficiency due to the streamlining of processes that would take a human significantly longer, such as locating and retrieving medication or identifying an active order in the system. Furthermore, although robots have seen increased use in pharmaceutical settings, such robots are extremely limited in their functionality, offering no counseling services and often unable even to navigate the whole of the pharmacy, being limited to a stationary role like that of a vending machine.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

Figure 1:
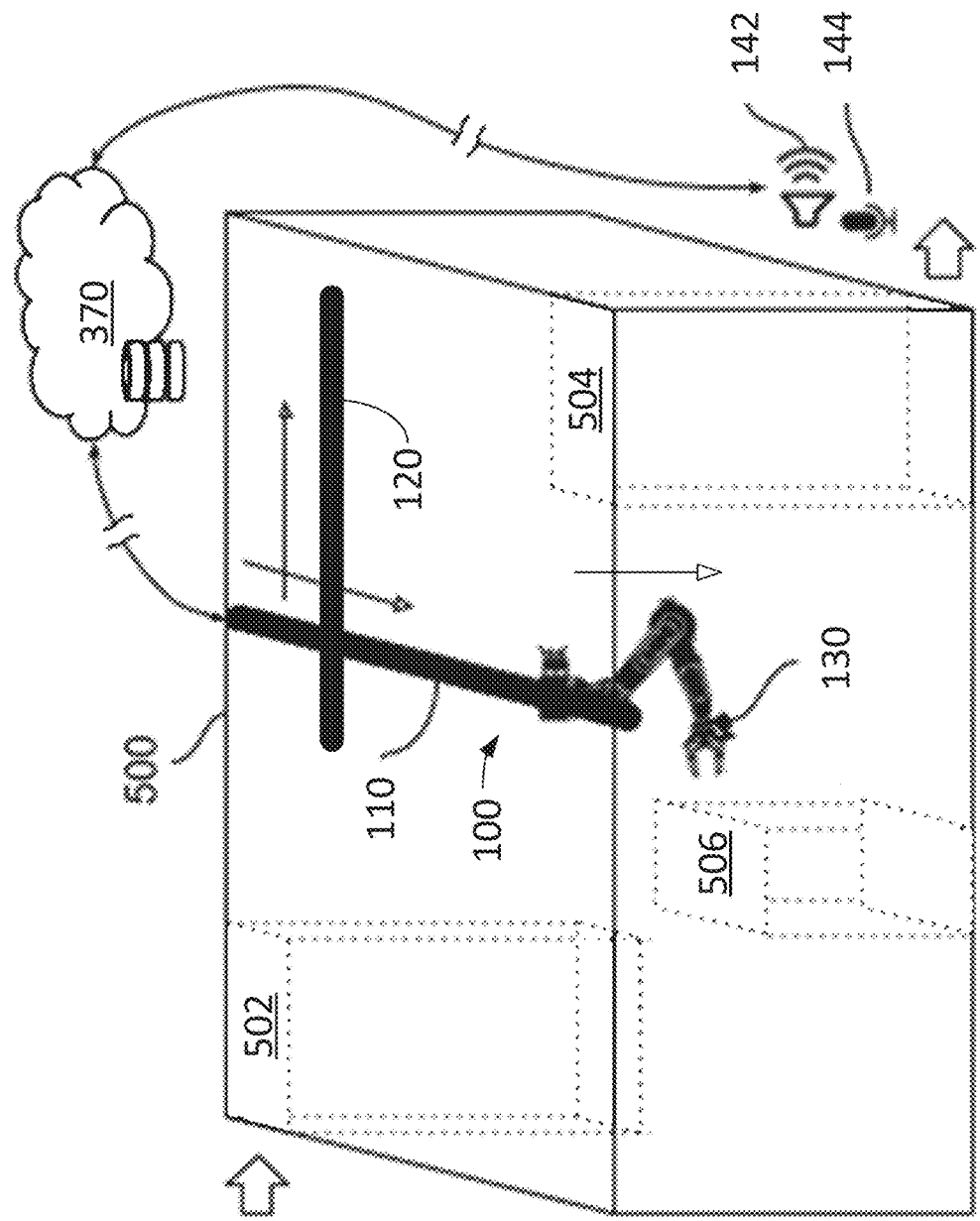
FIG. 1 shows a perspective view of a robotic pharmacy system, according to some arrangements.

FIG. 1 shows a perspective view of a robotic pharmacy system 10, according to some arrangements. As shown in FIG. 1, the robotic pharmacy system 10 includes a pharmacy robot 100, a speaker 142, a microphone array 144, a server 510, and a functional area 500. The pharmacy robot 100 further includes a first rail 110, a second rail 120, and a robotic arm 130. As shown, the robotic arm 130 may move in the x- and y-directions along the first rail 110 and the second rail 120 respectively in order to navigate the functional area 500. The robotic arm 130 may operate in the z-axis through movement of components (e.g., motors, joints, segments, etc.) of the robotic arm 130, as shown. Although the speaker 142 and microphone array 144 are shown in FIG. 1 as separate from the pharmacy robot 100, the speaker 142 and microphone array 144 may each be coupled to or located on the pharmacy robot 100 (e.g., on an end of the pharmacy robot 100). The pharmacy robot 100 may further include one or more optical sensory devices coupled to or located on the robotic arm. These one or more optical sensory devices may include a camera configured to detecting an object of interest (e.g., medicine bottle) as well as its position and orientation, or may include a range sensor configured to determine a distance between the robotic arm and an object (e.g., medicine bottle, shelf, etc.) In some embodiments, the optical sensor devices include devices with Light Detection and Ranging (LiDAR) functionality or sonar imaging to detect the ambient objects for collision avoidance.

The server 510 connects to the pharmacy robot 100 and provides instructions to the pharmacy robot 100. In some embodiments, the server 510 may be a physical computing system that connects to the pharmacy robot 100 via a wired or wireless connection (e.g., Ethernet, wireless Local Area Network (LAN), Wide Area Network (WAN), wireless data networks such as 4G, LTE, 5G, etc.), while in other embodiments, the server 510 may be a cloud-based computing system that is based remotely from the robotic pharmacy system 10 and connects to the pharmacy robot 100 via a network. In some embodiments, the pharmacy robot 100 is an actuator without a computer of its own, such that the pharmacy robot 100 is controlled completely by the server 510. In other embodiments, the pharmacy robot 100 further includes a computer that itself communicates with the server 510 and exercises some control over the pharmacy robot 100.

The functional area 500 is shown to include a supplying area 502, an aggregating area 504, and an internal storage device 506. The supplying area 502 may be a cabinet or shelf upon which objects (e.g., medicine bottles, medications, etc.) are stored and supplied. Although one supplying area is shown in FIG. 1, the supplying area 502 may include multiple supplying areas. The aggregating area 504 may be a surface or shelf upon which objects (e.g., filled medicine bottles) are placed for further processing. In some embodiments, there may be overlap between the supplying area 502 and the aggregating area 504, such that a single shelf serves as a supplying area 502 and an aggregating area 504. The internal storage device 506 may be a rack or cabinet that allows for storage of objects (e.g., filled medicine bottles) after or for further processing. For example, the internal storage device 506 may include one or more storage bins divided up by name or first letter of last name, and pharmacy robot 100 may place filled medicine bottles in the storage bins depending on the medication order.

Figure 2:
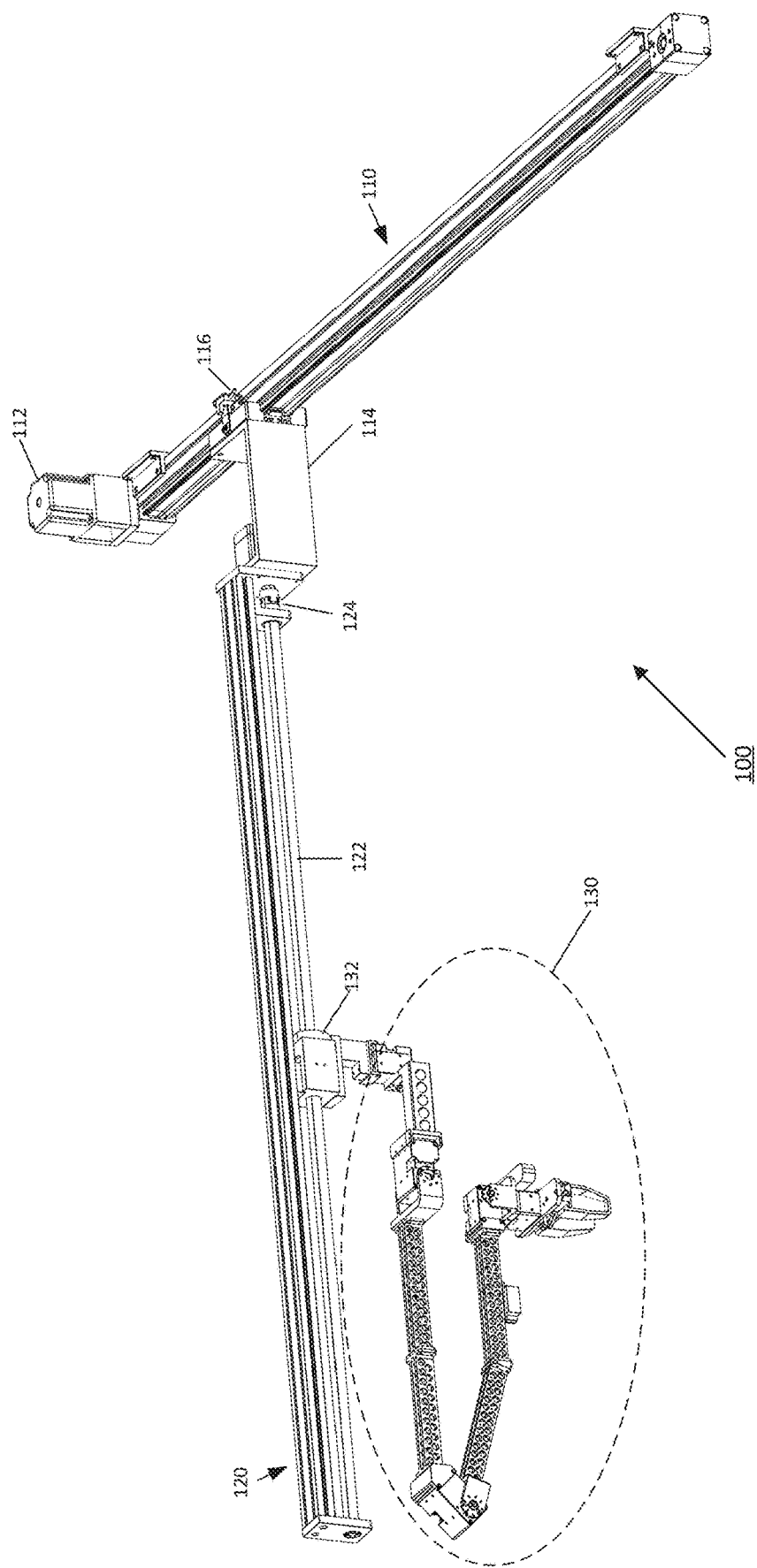
FIG. 2 shows a perspective view of a pharmacy service robot, according to some arrangements.

FIG. 2 shows a perspective view of the pharmacy robot 100 according to some arrangements. As shown, the pharmacy robot 100 may include the first rail 110, the second rail 120, and the robotic arm 130. The first rail 110 may be mounted to a wall or ceiling via a rail mount 112. In some embodiments, the first rail 110 is mounted to a standalone rack (not pictured) that supports the weight of the pharmacy robot 100 without a wall or ceiling. The second rail 120 is coupled to the first rail 110 via a rail coupling 114 that is structured to receive the second rail on one end and to attach to the first rail 110 on another end. The rail coupling 114 is further structured to move along the first rail 110 such that the second rail 120 may similarly move along the first rail 110. In some embodiments, the rail coupling 114 includes a motor or similar driver that provides a moving force for the rail coupling 114 (and thereby the second rail 120) to move or slide along the first rail 110. As such, the first rail 110 and the second rail enable movement of the robotic arm 130 along an x-axis and a y-axis. In some embodiments, a third rail (not pictured) is included in the pharmacy robot 100 in order to enable movement of the robotic arm 130 along a z-axis. The third rail may be coupled to the ceiling and the second rail 120, such that the second rail 120 moves along the z-axis, or coupled to the first rail 110 and the robotic arm 130, such that the robotic arm 130 moves along the z-axis. In other embodiments, movement along the z-axis is enabled by the robotic arm 130 itself, such that the entire robotic arm 130 does not move along the z-axis, but individual components of the robotic arm 130 (e.g., a jaw or manipulator) move along the z-axis via movement of other components of the robotic arm 130 (e.g., pivoting around joints, etc).

In some embodiments, such as the one shown in FIG. 2, a cord 116 is fed into the rail coupling 114. The cord 116 may be one or more of a power cord that powers the motor in the rail coupling 114 (if any) as well as any electric components in the second rail 120 or robotic arm 130 and a communications cord that provides a wired connection from a computer (e.g., the server 510, a standalone controller, etc.) to one or more components of the pharmacy robot 100.

The second rail 120 includes a rail runner 122 that runs along a length of the second rail 120 and provides a coupling point for the robotic arm 130 via an arm coupling 132. In some embodiments, the rail runner 122 is incorporated into the second rail 120 such that the second rail 120 is a single rail along which the arm coupling 132 can slide. In other embodiments, such as the one shown in FIG. 2, the rail runner 122 is a separate rail. The rail runner 124 may be individually (i.e., relative to the second rail 120) coupled to the rail coupling 114 via a rotational joint 124. The rotational joint 124 is structured to provide a rotational force to the rail runner 122 (e.g., via the motor included within the rail coupling 114) in order to increase the range of motion of the robotic arm 130 by allowing rotation about an axis formed by the rail runner 122. In some embodiments, the rotational joint 124 may be omitted (such that the rail runner 122 is fixedly coupled to the rail coupling 114).

Figure 3:
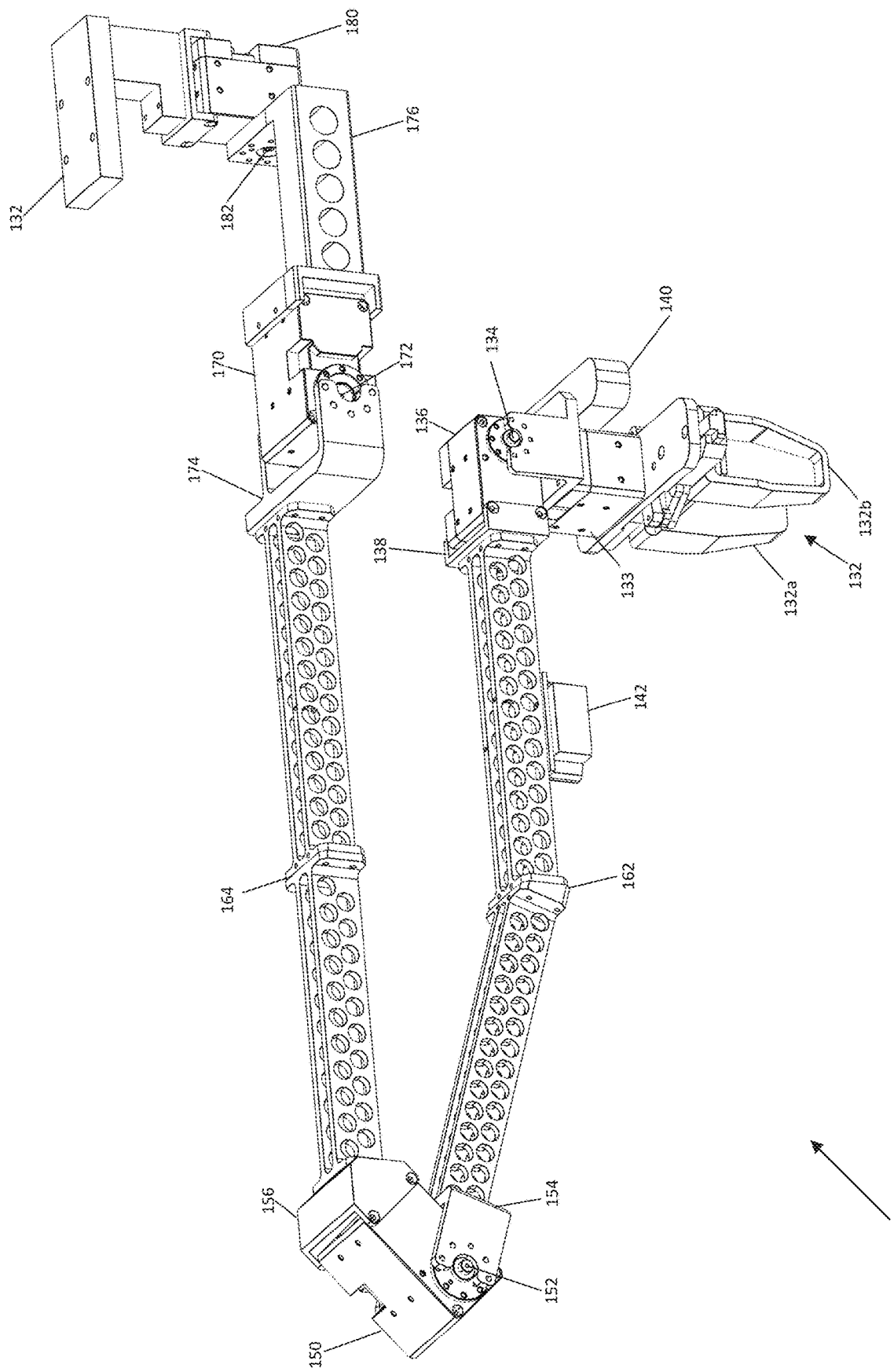
FIG. 3 shows a perspective view of a robotic arm, according to some arrangements.

The robotic arm 130 is shown in greater detail in FIG. 3. As shown in FIG. 3, the robotic arm 130 includes a jaw 132, a first segment 162, a secondary joint 150, a second segment

164, and a primary joint 170. The jaw 132 (also referred to as a "manipulator" or "robotic manipulator") includes a first mandible 132*a* and a second mandible 132*b*, each of which is structured to move along an axis perpendicular to the faces of the first mandible 132*a* and the second mandible 132*b*. In this way, the first mandible 132*a* and the second mandible 132*b* can move towards each other to apply counter-forces upon an object (e.g., a pill bottle) in order to grab the object. In some embodiments, the first mandible 132*a* and second mandible 132*b* may move independently of each other, such that one mandible is stationary while the other moves in order to apply a grabbing force to an object. The first mandible 132*a* and second mandible 132*b* are coupled to a first jaw block 133, which includes a mechanism for moving the first mandible 132*a* and second mandible 132*b*. For example, the first jaw block 133 may include an electric motor (receiving power by the cord 116) that provides a moving force to at least one of the first mandible 132*a* or the second mandible 132*b* in order to move the first mandible 132*a* and second mandible 132*b* and provide the grabbing force. In another example, the first jaw block 133 includes a series of gears that receive a powering force from a separate motor (i.e., elsewhere in the pharmacy robot 100) and translate that force to move the first mandible 132*a* and second mandible 132*b*.

The first jaw block 133 is coupled to a second jaw block 136 via a jaw joint 134. The second jaw block 136 may include a motor to power one or more of the jaw joint 134, the first jaw block 133, the first mandible 132*a*, and the second mandible 132*b*. The jaw joint 134 includes an axle around which the jaw 132 rotates. The second jaw block 136 is coupled to the first segment 162 via a jaw coupling 138.

As shown in FIG. 3, the first segment 162 includes two separate segments joined at an obtuse angle in order to form a crooked segment. In other embodiments, the first segment 162 is formed by a single straight segment or by two separate segments joined at a straight angle to form a straight segment. The first segment 162 connects the jaw 130 (via the jaw coupling 138) to the secondary joint 150 (via a first secondary joint coupling 154). The first secondary joint coupling 154 is coupled to the secondary joint 150 via a secondary joint axle 152, which provides a rotational force to the first secondary joint coupling 154, thereby rotating the first segment 162 (and jaw 132, etc.) about an axis formed by the secondary joint axle 152. The secondary joint 150 may include a motor (or analogous mechanism) to generate the rotational force about the secondary joint axle 152. As such, in general terms, the secondary joint 150 extends the operational range of the jaw 132 by enabling the first segment 162 and all attached components (including the jaw 132) to rotate about the axis formed by the secondary joint axle 152.

The secondary joint 150 is coupled to the second segment 164 via a second secondary joint coupling 156, which fixedly couples the secondary joint 150 to the second segment 164 (in contrast to the first secondary joint coupling 154 that rotatably couples the first segment 162 to the secondary joint 150). As shown in FIG. 3, the first segment 162 includes two separate segments joined at a straight angle in order to form a straight segment. In other embodiments, the second segment 164 is formed by a single straight segment or by two separate segments joined at an obtuse angle to form a crooked segment.

The second segment 164 connects the secondary joint 150 (via the first secondary joint coupling 154) to the primary joint 170 (via a first primary joint coupling 174). The first primary joint coupling 174 is coupled to the primary joint 170 via a primary joint axle 172, which provides a rotational force to the first primary joint coupling 174, thereby rotating the second segment about an axis formed by the primary joint axle 172. The primary joint 150 may include a motor (or analogous mechanism) to generate the rotational force about the primary joint axle 172. As such, in general terms, the primary joint 170 extends the operational range of the jaw 132 by enabling the second segment 164 and all attached components (including the jaw 132) to rotate about the axis formed by the primary joint axle 172.

The primary joint 170 is fixedly coupled to an arm block 180 via a second primary joint coupling. The arm block 180 includes the arm coupling 132, which connects the robotic arm 130 to the second rail 120 as described herein with reference to FIG. 2. As such, the arm block 180 may include a motor (or analogous mechanism) that provides power to the arm coupling 132 to move the arm coupling 132 along the second rail.

The robotic arm 130 includes a camera 140 and a speaker 142. As shown in FIG. 3, the camera 140 is fixed to the first jaw block, and the speaker 142 is fixed to the first segment. However, the camera 140 and speaker 142 may be fixed in any suitable location (e.g., the camera 142 fixed to the arm block 180, the speaker 142 fixed to the secondary joint 150, etc.) Furthermore, although the camera 140 is shown to be a single camera and the speaker 142 is shown to be a single speaker, multiple cameras and multiple speakers may be located throughout the pharmacy robot 100. Use of multiple cameras in particular may be technologically advantageous in order to provide a more complete picture of the surroundings of the pharmacy robot 100. Furthermore, the robotic arm 130 may include one or more sensors (e.g., range sensors, distance sensors, etc.) that are configured to generate signals that the pharmacy robot 100 can interpret to better provide a picture of the surrounding of the pharmacy robot 100 and/or to determine a position of the robotic arm 130 relative to an object (e.g., a pill bottle).

The camera 140 is structured to generate optical signals indicative of objects in the field of vision of the camera 140 and to transmit those optical signals to an arm computer 310 or analogous computing device. The arm computer 310 is described in greater detail in FIG. 5. The optical signals may indicate a presence of one or more people in the vicinity of the pharmacy robot 100, may include data about facial features of the one or more people (e.g., for identification and/or verification), and may include data about characteristics of one or more pill bottles (e.g., medication name, dosage, prescribing doctor, prescribed person, etc.). The speaker 142 is structured to receive signals from the arm computer 310 and to broadcast sounds and audio according to the signals. For examples, the arm computer 310 may send signals to the speaker 142 that command the speaker 142 to broadcast a welcome message to a person who enters the vicinity of the pharmacy robot 100.

In some embodiments, robotic arm 130 further includes a microphone array 144 that is structured to receive sound or audio (e.g., from people identifying themselves) and to transmit signals indicative of that received sound to the arm computer 310. The microphone array 144 may include one or more microphones, and may be located anywhere on or in the robotic arm 130 in order to best capture sound from customers entering the pharmacy. As such, the one or more microphones may be positioned in such a way that from the microphone or an array of microphones, a direction of customer arrival can be determined by the arm computer 310 based on sound received from the customer. To this end, an exterior of the pharmacy robot 100 may feature various openings and/or holes that guide acoustic waves of sounds (e.g., the sound of a customer arriving) towards the microphone array 144. The resulted direction of arrival may guide the pharmacy robot 100 to face the customer. In one example, the microphone array 144 is included with the camera 140 because both components work best when directed at a customer. In another example, the microphone array 144 is located in a separate location from the robotic arm 130 (e.g., by a counter of the pharmacy), such that signals from the microphone array 144 are still sent to the arm computer 310 but the microphone array 144 itself is not located on the robotic arm.

In further embodiments, the pharmacy robot 100 includes other devices or components structured to receive data from a customer and transmit signals indicative of that data to the arm computer 310. These other devices may include a biometric device (e.g., thumb scanner) that is structured to receive biometric data from a customer via physical touch, or these other devices may include an input/output device (e.g., a tablet, computer with keyboard, etc.) that is structured to receive a typed input from a customer, such as a name or account identifier. The input/output device may also be structured to display communication from the arm computer 310 (i.e., in accordance with or instead of the speaker 142).

Figure 4:
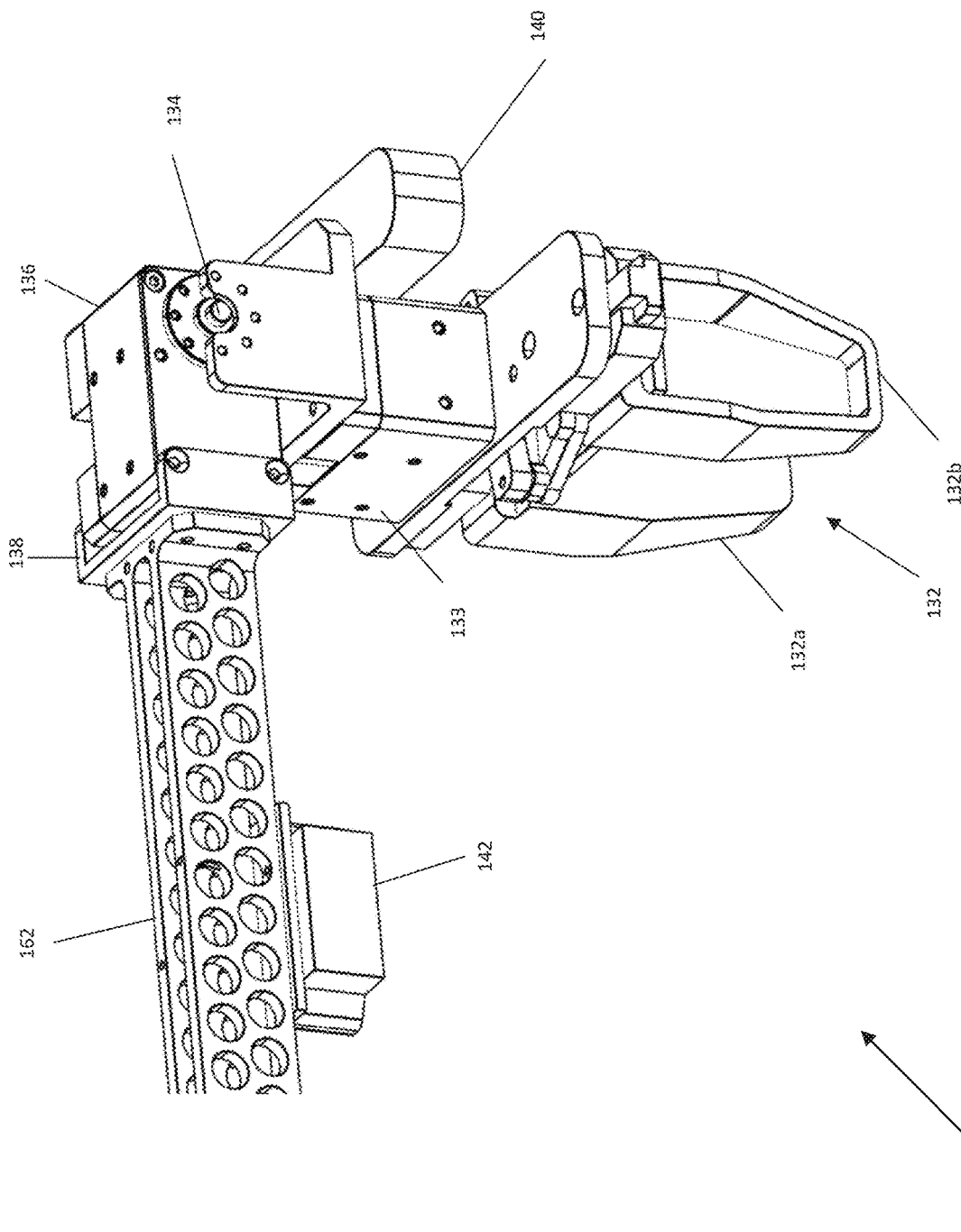
FIG. 4 shows a perspective view of a jaw of the robotic arm of FIG. 3, according to some arrangements.

FIG. 4 shows a perspective view of the robotic arm 130 of FIG. 3, according to some arrangements. Specifically, FIG. 4 shows an enlarged view of the jaw 132. In some embodiments, the end manipulator includes a tactile senor, force sensor, or sensors at the jaw 132. This sensor signal feeds back to the arm computer 310 for closing position control of the jaw 132 without damaging the package of the objects. The shape of the jaw as concave surfaces enhances the stability for gripping bottles or other round objects. However, in other embodiments, the jaw 132 of the robotic arm 130 can be replaced by other end manipulators (e.g., an anthropomorphic hand with different finger configurations, a hook, etc.).

Figure 5:
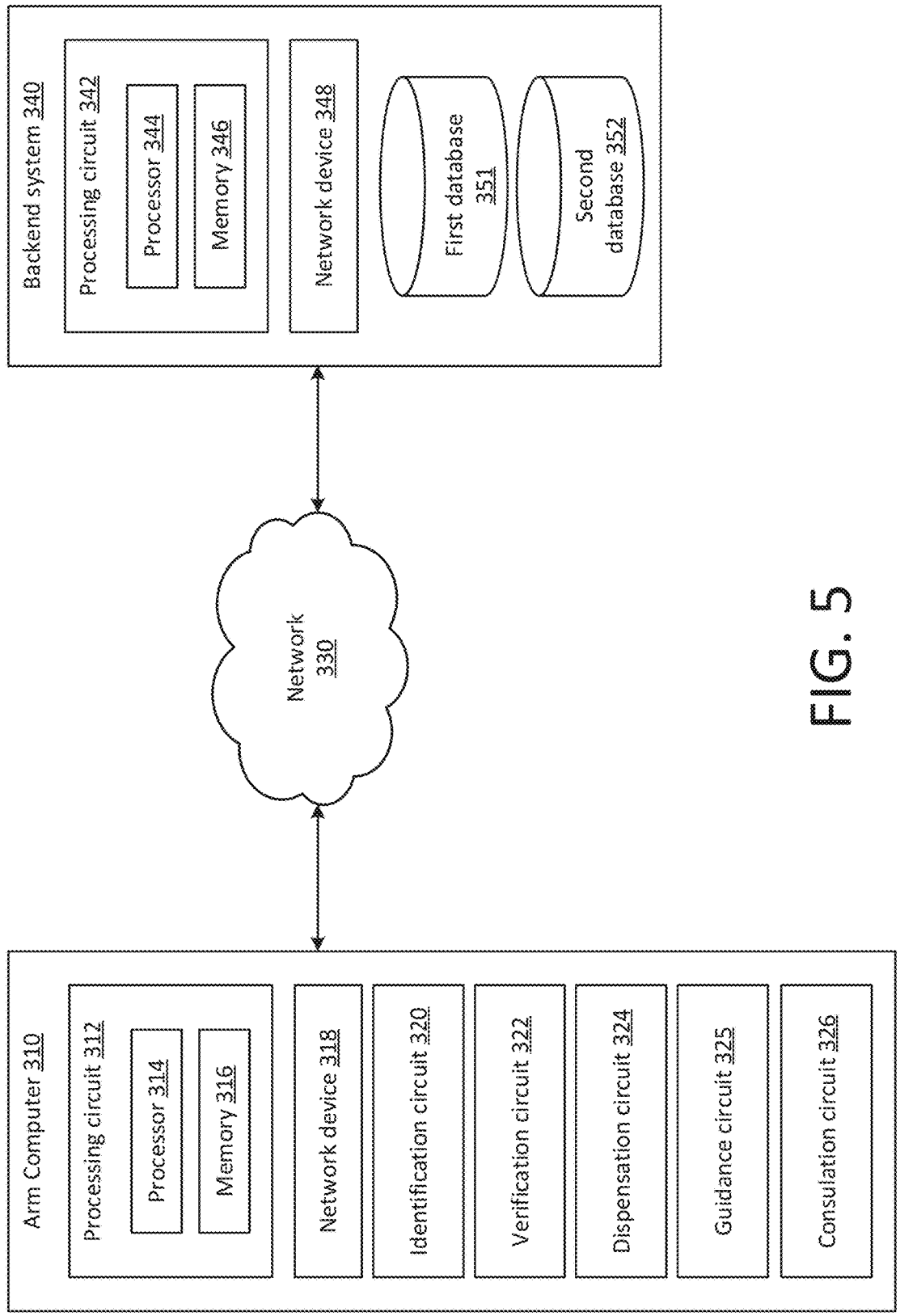
FIG. 5 is a block diagram of a system for operating the pharmacy robot of FIG. 2, according to some arrangements.

FIG. 5 is a diagram of a system 300 for identifying, verifying, and servicing a pharmacy customer, according to some arrangements. Referring to FIG. 5, the system 300 includes at least an arm computer 310 and a backend system 340. Each of the arm computer 310 and the backend system 340 is a computing system having suitable processing, storage, and networking capabilities. In some arrangements, the backend system 340 can be connected to the arm computer 310 via a network 330 as shown. Generally, in the system 300, the arm computer 310 or the backend system 340 can be configured to identify, verify, and service the pharmacy customer in the manner described.

The arm computer 310 is connected to the backend system 340 via a network 330. The network 330 is any suitable Local Area Network (LAN) or Wide Area Network (WAN). For example, the network 330 can be supported by Frequency Division Multiple Access (FDMA), Time Division Multiple Access (TDMA), Code Division Multiple Access (CDMA) (particularly, Evolution-Data Optimized (EVDO)), Universal Mobile Telecommunications Systems (UMTS) (particularly, Time Division Synchronous CDMA (TD-SCDMA or TDS) Wideband Code Division Multiple Access (WCDMA), Long Term Evolution (LTE), evolved Multimedia Broadcast Multicast Services (eMBMS), High-Speed Downlink Packet Access (HSDPA), and the like), Universal Terrestrial Radio Access (UTRA), Global System for Mobile Communications (GSM), Code Division Multiple Access 1x Radio Transmission Technology (1x), General Packet Radio Service (GPRS), Personal Communications Service (PCS), 802.11X, ZigBee, Bluetooth®, Wi-Fi, any suitable wired network, combination thereof, and/or the like. The network 330 is structured to permit the exchange of data, values, instructions, messages, and the like between the arm computer 310 and the backend system 340.

The arm computer 310 can be any suitable computing device configured to process signals from the camera 140, other optical sensors (e.g., LiDAR, Sonar sensors) and microphone array 144, receive relevant information from the backend system 340, and command the robotic arm 100 in accordance with the received signals and information. In some embodiments, the arm computer 310 is included in the robotic arm 100 such that hardware of the arm computer 310 is physically mounted to the robotic arm 100. In other embodiments, the hardware of the arm computer 310 is physically separate from the robotic arm 100 and communicates with the robot arm either over a network (e.g., the network 330) or via a wired connection (e.g., the cord 116).

The arm computer 310 is shown to include a processing circuit 312 having a processor 314 and a memory 316, a network device 318, an identification circuit 320, a verification circuit 322, a dispensation circuit 324, a guidance circuit 325, and a consultation circuit 326. Generally, the arm computer 310 is structured to receive and process information regarding a pharmacy and command various components of the pharmacy robot 100 in order to operate the pharmacy.

In one configuration, the identification circuit 320, the verification circuit 322, the dispensation circuit 324, guidance circuit 325, and the consultation circuit 326 are embodied as machine or computer-readable media storing instructions that are executable by a processor, such as processor 314. As described herein and amongst other uses, the machine-readable media facilitates performance of certain operations to enable reception and transmission of data. For example, the machine-readable media may provide an instruction (e.g., command, etc.) to, e.g., acquire data. In this regard, the machine-readable media may include programmable logic that defines the frequency of acquisition of the data (or, transmission of the data). The computer readable media instructions may include code, which may be written in any programming language including, but not limited to, Java or the like and any conventional procedural programming languages, such as the "C" programming language or similar programming languages. The computer readable program code may be executed on one processor or multiple remote processors. In the latter scenario, the remote processors may be connected to each other through any type of network (e.g., CAN bus, etc.).

In some embodiments, the identification circuit 320, the verification circuit 322, the dispensation circuit 324, the guidance circuit 325, and the consultation circuit 326 may take the form of one or more analog circuits, electronic circuits (e.g., integrated circuits (IC), discrete circuits, system on a chip (SOCs) circuits, microcontrollers, etc.), telecommunication circuits, hybrid circuits, and any other type of "circuit." In this regard, the identification circuit 320, the verification circuit 322, the dispensation circuit 324, the guidance circuit 325, and the consultation circuit 326 may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on). The identification circuit 320, the verification circuit 322, the dispensation circuit 324, the guidance circuit 325, and the consultation circuit 326 may also include programmable hardware devices such as field programmable gate arrays, programmable array logic, programmable logic devices or the like. The identification circuit 320, the verification circuit 322, the dispensation circuit 324, the guidance circuit 325, and the consultation circuit 326 may include one or more memory devices for storing instructions that are executable by the processor(s) of the identification circuit 320, the verification circuit 322, the dispensation circuit 324, the guidance circuit 325, and the consultation circuit 326.

In the example shown, the arm computer 310 includes the processing circuit 312 having the processor 314 and the memory 316. The processing circuit 312 may be structured or configured to execute or implement the instructions, commands, and/or control processes described herein with respect to the identification circuit 320, the verification circuit 322, the dispensation circuit 324, the guidance circuit 325, and the consultation circuit 326. The depicted configuration represents the identification circuit 320, the verification circuit 322, the dispensation circuit 324, the guidance circuit 325, and the consultation circuit 326 as machine or computer-readable media storing instructions. However, as mentioned above, this illustration is not meant to be limiting as the present disclosure contemplates other embodiments where the identification circuit 320, the verification circuit 322, the dispensation circuit 324, the guidance circuit 325, and the consultation circuit 326, or at least one circuit of the identification circuit 320, the verification circuit 322, the dispensation circuit 324, the guidance circuit 325, and the consultation circuit 326, is configured as a hardware unit. All such combinations and variations are intended to fall within the scope of the present disclosure.

The processor 314 may be implemented as a single- or multi-chip processor, a digital signal processor (DSP), an application specific integrated circuit (ASIC), a field programmable gate array (FPGA), a Graphics Processing Unit (GPU) or other programmable logic device, discrete gate or transistor logic, discrete hardware components, or any combination thereof designed to perform the functions described herein. A processor may be a suitable processor, a microprocessor, a group of processors, etc. A processor also may be implemented as a combination of computing devices, such as a combination of a DSP and a microprocessor, a plurality of microprocessors, one or more microprocessors in conjunction with a DSP core, or any other such configuration. In some embodiments, the one or more processors may be shared by multiple circuits (e.g., the identification circuit 320, the verification circuit 322, the dispensation circuit 324, the guidance circuit 325, and the consultation circuit 326 may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. All such variations are intended to fall within the scope of the present disclosure.

The memory 314 (e.g., memory unit, storage device) may include one or more devices (e.g., RAM, ROM, Flash memory, hard disk storage) for storing data and/or computer code for completing or facilitating the various processes, layers and modules described in the present disclosure. The memory 314 may be communicably connected to the processor 312 to provide computer code or instructions to the processor 312 for executing at least some of the processes described herein. Moreover, the memory 314 may be or include tangible, non-transient volatile memory or non-volatile memory. Accordingly, the memory 314 may include database components, object code components, script components, or any other type of information structure for supporting the various activities and information structures described herein.

The arm computer 310 includes a processing circuit 312 having a processor 314 and a memory 316. The processor 314 can be implemented as a general-purpose processor, an Application Specific Integrated Circuit (ASIC), one or more Field Programmable Gate Arrays (FPGAs), a Graphics Processing Unit (GPU), a Digital Signal Processor (DSP), a group of processing components, or other suitable electronic processing components. The memory 316 (e.g., Random Access Memory (RAM), Read-Only Memory (ROM), Non-volatile RAM (NVRAM), flash memory, hard disk storage, etc.) stores data and/or computer code for facilitating at least some of the various processes described herein. The memory 316 includes tangible, non-transient volatile memory, or non-volatile memory. The memory 316 can include a non-transitory processor readable medium having stores programming logic that, when executed by the processor 314, controls the operations of the arm computer 310.

The network device 320 is structured for sending and receiving data over the network 330 (e.g., to and from the backend system 340 and one or more other suitable devices). Accordingly, the network device 320 includes any of a cellular transceiver (for cellular standards), local wireless network transceiver (for 802.11X, ZigBee, Bluetooth, Wi-Fi, or the like), wired network interface, a combination thereof (e.g., both a cellular transceiver and a Bluetooth transceiver), and/or the like.

The backend system 340 can be a computing system that collects data for customers/patients of a pharmacy, maintains one or more databases containing the collected data, generates data analytics, and provides data on request from the arm computer 310. The backend system 340 includes a processing circuit 342 having a processor 344 and a memory 346. The processor 144 is implemented as a general-purpose processor, an ASIC, one or more FPGAs, a DSP, a group of processing components, or other suitable electronic processing components. The memory 346 (e.g., RAM, ROM, NVRAM, flash memory, hard disk storage, etc.) stores data and/or computer code for facilitating at least some of the various processes described herein. The memory 346 includes tangible, non-transient volatile memory, or non-volatile memory. The memory 346 can include a non-transitory processor readable medium having stores programming logic that, when executed by the processor 344, controls the operations of the backend system 340. In some embodiments, the backend system 340 is a remote or cloud-based computing system, such that the processor 344 is a remote processor and the memory 346 is a remote memory. In this regard, a given circuit or components thereof can be disposed locally (e.g., as part of a local server, a local computing system, etc.) or remotely (e.g., as part of a remote server such as a cloud based server). To that end, a "circuit" as described herein for the backend system 340 can include components that are distributed across one or more locations.

As shown, the backend system 340 includes a network device 348. The network device 348 is structured for sending and receiving data over the network 330 (e.g., to and from the arm computer 310, etc.). Accordingly, the network device 348 includes any of a cellular transceiver (for cellular standards), local wireless network transceiver (for 802.11X, ZigBee, Bluetooth®, Wi-Fi, or the like), wired network interface, a combination thereof (e.g., both a cellular transceiver and a Bluetooth transceiver), and/or the like.

The backend system 340 includes a first database 351 and a second database 352. The first database 351 stores general customer information related to identification and verification of customers. For example, the first database 351 may include an address, a birthdate, an emergency contact, a phone number, and/or an email address associated with a customer. The first database 351 may also contain biometric information associated with a customer. The biometric information can be used for identification or verification and may include a facial profile, a voice profile, etc. The biometric information may be requested from a customer prior to arrival at the pharmacy or may be received from the customer upon arrival. In embodiments in which pharmacy customers are associated with an account (e.g., loyalty account), the first database 351 may further include account information relating to accounts held by customers with a pharmacy, including an account number. In some embodiments, the account information further includes information regarding a payment method (e.g., debit card number, credit card number, bank account number, etc.) that is kept stored in order to facilitate payment upon pickup by a customer. As described herein, the first database 351 stores information that is either public or near-public, such that the information is likely available to the public without privileged access or is not required to be protected by law (e.g., Health Insurance Portability and Accountability Act (HIPAA)).

The second database 352 stores sensitive customer information related to customers' health histories, prescriptions, and other information that is required by law to be maintained with additional security. This information may be received directly from a customer (e.g., entered in an online form, spoken in response to a request for information from the speakers 142, etc.) or may be transferred to the backend system 340 via a third party. For example, a doctor's office may transfer medical records and an e-prescription for a patient. These transfers are performed in accordance with all relevant laws (e.g., 21 C.F.R. § 1306.08). As such, the second database 352 may store information related to a particular customer's medication history, along with any associated side effects (if any), which can be utilized by the backend system 340 (or arm computer 310) to provide consultation to the particular customer. In those embodiments in which pharmacy customers are associated with an account, the second database 352 may associate the sensitive customer information with an account number rather than a customer's name in order to provide an additional layer of security through abstraction. Due to the sensitive nature of the information stored in the second database 352, the first database 351 and the second database 352 may be maintained separately, which may entail maintaining the first database 351 and the second database 352 on physically separate memory devices or partitioning the memory 346 to host the first database 351 and the second database on the same memory 346 but with the ability to enforce different security measures. In some embodiments, the first database 351 and the second database 352 are a single database with security measures sufficient for the sensitive information.

In some embodiments, the backend system 340 is configured to leverage the data collected and stored in the first database 351 and second database 352 to form profiles of customers that can be analyzed and provided to one or more third parties. Due to the often sensitive nature of some of this stored data (particularly those data in the second database 352), any disclosure of information would be in full compliance with the relevant laws and regulations (e.g., HIPAA). For the less sensitive data (i.e., data that is borderline public), such as geolocation, age, sex, or ethnicity, or for the less identifying data (i.e., data that may not identify an individual without additional context), such as disease history or current illness, the backend system 340 may provide statistical analysis that can be useful for marketing (e.g., demographics for advertisement sales) or research (e.g., phase IV medication studies) purposes. In this way, the backend system 340 is providing a Software as a Service (SaaS) model.

Referring again to the arm computer 310, the identification circuit 320 is structured or configured to receive one or more signals regarding a customer, compare data from the one or more signals to customer information stored in the backend system 340, and determine an identity of the customer. The one or more signals may include optical signals from the camera 140 or audio signals from the microphone array 144. For example, if a customer enters the pharmacy (or a service area of the pharmacy robot 100), the camera 140 generates an optical signal indicative of the customer's appearance, and the identification circuit 320 receives that optical signal. In another example, if a customer enters the pharmacy (or the service area of the pharmacy robot 100) and states "I'm John Doe and here to pick up my prescription," the microphone array 144 generates an audio signal indicative of the statement, and the identification circuit 320 receives that audio signal. The identification circuit 320 can then process the signal in order to distill the identifying data contained within the signal.

From there, the identification circuit 320 compares the identifying data to information stored in the first database 351. In some embodiments, the identification circuit 320 requests a pool of information from the backend system 340 and compares the identifying data to that pool of information. The request may be based on currently active orders (i.e., orders for medication that have been received but not completed or picked up), such that the identification circuit 320 requests information for all customers with currently active orders, or may be based on active actives (i.e., customer accounts that have been set up or confirmed), such that the identification circuit 320 requests information for all customers with active accounts. In other embodiments, the identification circuit 320 sends the identifying data to the backend system 340 and the backend system 340 performs the comparison (rather than the identification circuit 320). In these embodiments, the comparison can be made to all of the customer information in the first database 351, but then requires an additional step of receiving, from the backend system 340, results of the comparison.

If the comparison results in a match (i.e., the identifying data matches with at least one set of information from the backend system 340 at a high percentage level of tolerance), the identification circuit 320 determines an identity of the customer as a user associated with the matched information. For example, if the identifying data distilled from optical data matches a facial profile, the identification circuit 320 identifies the customer as the customer associated with the facial profile.

However, if the comparison does not result in a match within the requested pool of information, the identification circuit 320 may request additional information from the backend system 340 (i.e., broaden the requested pool of information beyond active orders and accounts) or may offer to the customer an opportunity to open an account. For example, if the customer has a prescription from a doctor but did not send the prescription directly to the pharmacy, the customer is unlikely to have an account or any information stored in the backend system 340, and the lack of match is an opportunity to enter the customer and the customer's information into the backend system 340. In some embodiments, the opportunity to open an account may be presented as an audio offer from the speaker 142, and may include an invitation to orally provide relevant information, to fill out a form that is subsequently scanned into the system, or to provide an email address to which the arm computer 310 (or backend system 340) can send an email with account setup instructions.

The verification circuit 322 is structured or configured to receive information from a customer, compare the information to information associated with the customer and stored in the backend system 340, and verify the customer as authorized for pickup. In some embodiments, the verification circuit 322 replaces the identification circuit 320 such that the verification circuit 322 is both identifying and verifying users. In other embodiments, the verification circuit 322 supplements the identification circuit 320 by verifying those users the identification circuit 320 has identified (e.g., for additional security, to confirm an associated account, etc.). In further embodiments, the verification circuit 322 supplements the identification circuit 320 by verifying customers who are not matched by the identification circuit 320. For example, if a husband is picking up his wife's medication, the husband is not identified as the wife but can be verified by the verification circuit 322 as authorized to pick up his wife's medication. In some embodiments, the verification circuit 322 is skipped or omitted, such that the customer is authorized for pickup upon identification by the identification circuit.

The verification circuit 322 first receives information from a customer. This information may be the biometric information utilized by the identification circuit 320, or may be other information related to the customer, such as an address, phone number, or email address of the customer. The verification circuit 322 may request this information (e.g., via the speaker), and may request specific information (e.g., "Please provide your home address for verification.") or may generally request information for verification. In those embodiments in which the verification circuit 322 is supplementing the identification circuit 320, the verification circuit 322 may specifically request information that satisfies a something-you-know condition to go along with the something-you-are condition satisfied by the biometric information.

In some embodiments, and in particular those embodiments in which the verification circuit 322 is verifying a non-matched customer, the verification circuit 322 may specifically request information of the type stored in the second database 352. Because the type of information stored in the second database 352 is more private, it is less likely to be known by an unassociated third party. As such, knowledge of this type of information provides a stronger something-you-know factor as compared to knowing information of the type stored in the first database 351. This can be especially important if the customer is not matched by the identification circuit 320. Returning to the example of the husband picking up his wife's medication, the husband offering knowledge of his wife's medical allergies (which are likely only known to close family) is more dispositive of his status as an authorized person than the husband offering knowledge of his wife's birthday (which is likely known to anyone with access to her social media).

Similarly to the identification circuit 320, the verification circuit 322 compares the verifying information provided by the customer to information stored by the backend system 340. In those embodiments in which the verification circuit 322 is verifying an identified customer (i.e., the customer was matched by the identification circuit 320), the verification circuit 322 requests information from the backend system 340 that corresponds to the identified customer and compares the verifying information to that requested information. In other embodiments, the verification circuit 322 sends the verifying information to the backend system 340 and the backend system 340 performs the comparison (rather than the verification circuit 322). Particularly in those embodiments in which the requested information is of the type stored in the second database 352, avoiding sending secure information over the network 330 may be inadvisable, so the verification circuit 322 sends the verifying information to the backend system 340 so that the information stored in the second database 352 is not transmitted over the network 330. Although the verifying information is still sent over the network 330, there is less of a security concern than for sending the information stored in the second database 352, which is subject to HIPAA and other protective laws.

In response to the verifying information matching information stored by the backend system 340, the verification circuit 322 determines that the customer is authorized to pick up the related medication. In those embodiments in which the verification circuit 322 is verifying an identified customer in order to confirm the customer's account, the verification circuit 322 can annotate the customer's account (e.g., add a note to the account information stored in the backend system 340) such that the verification circuit 322 does not attempt to verify the customer on subsequent visits. In those embodiments in which the verification circuit 322 is verifying a non-matched customer (i.e., the husband picking up wife's medications), the verification circuit 322 can offer (e.g., via the speaker 142) to add the unmatched customer to the associated account (e.g., add a note to the account information stored in the backend system 340).

The dispensation circuit 324 is structured or configured to associate a customer with an active medication order, determine a status of the medication order, and dispense the medication if the medication order is ready. Once the customer has been authorized to pick up medication (by the identification circuit 320 and/or verification circuit 322), the dispensation circuit 324 matches the customer (or the individual for whom the customer is authorized to pick up medication) with an active medication order. This association may be performed by matching a name of the customer (or individual related to customer) with the name on the active medication order (i.e., the person for whom the medication is prescribed), or may be performed by matching an account identifier of the customer with the account identifier associated with the active medication order.

Once the dispensation circuit 324 has matched the customer with an active medication order, the dispensation circuit 324 determines if the medication order is ready (i.e., the prescription is filled). In some embodiments, the dispensation circuit 324 compares the active medication order to a list of ready medication orders that is maintained and updated as orders are filled. For example, if a human pharmacy worker is filling medication orders, the pharmacy worker may update a spreadsheet (or similar tracking system) to reflect medication orders that have been filled. In another example, the backend system 340 may maintain an inventory of medications, including an order status of medications (i.e., filled or unfilled) or an expiration status of medications (i.e., whether the medication is past its usable date based on the National Drug Code). If the medication order is not ready, the dispensation circuit 324 either requests a human pharmacy worker to fill the order or issues commands to the robotic arm 130 to fill the order. These commands may include instructions on identifying the relevant medication using the camera 140, manipulating a bottle or canister to receive medication, meting out a quantity of medication, and sealing and labeling the bottle. In some embodiments, such as those in which there is no human pharmacy worker to fill prescriptions, the dispensation circuit 324 does not check for readiness and proceeds directly to filling the order.

Once the order is ready and filled, the dispensation circuit 324 communicates with the guidance circuit 325 to locate the filled order and gives the filled order to the customer. In those embodiments in which the dispensation circuit 324 commanded the robotic arm 130 to fill the order in response to the customer arriving, the filled order is being held by the robotic arm (e.g., in the jaw 132), so the dispensation circuit 324 may skip the location step and instead command the robotic arm 130 to manipulate the filled order to a designated area (e.g., a dispensary shelf). In those embodiments in which the order was filled prior to the customer's arrival or filled by the worker (i.e., the filled order is not already being held by the robotic arm 130), the dispensation circuit 324 utilizes location and positioning data from the guidance circuit to locate the filled order. Once the filled order has been located, the dispensation circuit 324 commands the robotic arm 130 to manipulate the filled order to the designated area for customer pickup.

Commanding the robotic arm 130 to manipulate the filled order includes commands to individual motors throughout the robotic arm 130 that can work together to control the individual components of the robotic arm 130. In one example, the dispensation circuit 324 first commands motors in the second jaw block 136, the secondary joint 150, and the primary joint 170 to position the jaw 132 in front of the filled order. The dispensation circuit 324 may also issue commands to the first rail 110 and the second rail 120 if necessary to position the robotic arm 130. Once the robotic arm 130 is in position, the dispensation circuit 324 commands the jaw 132 to open (i.e., move the first mandible 132a and the second mandible 132b apart) by commanding a motor in the first jaw block 133. After issuing commands to move the jaw 132 towards the filled order such that the first mandible 132a is on one side of the filled order and the second mandible 132b is on another side of the filled order, the dispensing circuit 224 issues commands to the jaw 132 to close on the filled order. From there, the dispensation circuit 324 issues commands to the motors in the second jaw block 136, the secondary joint 150, and the primary joint 170 (an optionally the first rail 110 and the second rail 120) such that the robotic arm 130 manipulates the filled order to a designated area for customer pickup. Finally, the dispensation circuit 324 commands the motor in the first jaw block 133 to open the jaw 132 (i.e., move the first mandible 132a and the second mandible 132b away from each other) to release the filled order.

The guidance circuit 325 is structured or configured to use optical data from the camera 140 and/or data from the one or more sensors (e.g., LiDAR, sonar) to determine a position of the object and to facilitate movement of the robotic arm 130 to a position proximate to the object. For example, the filled order may have a barcode (or similar visual identifier) on a label on the object (e.g., bottle), and the guidance circuit 325 locates the object based on the camera 140 detecting the barcode. In some embodiments, the guidance circuit 325 commands the robotic arm 130 to move along shelves of filled orders until the camera 140 detects the barcode. In some embodiments, locations of filled orders are logged in the backend system 340 (e.g., "Shelf 2, slot 10"), and the guidance circuit 325 locates the filled order by consulting the stored location.

Once the guidance circuit 325 has identified or located the object, the guidance circuit 325 facilitates movement of the robotic arm 130 to a position at which the robotic arm 130 is able to grasp the object (e.g., via the jaw 132). In some embodiments, the guidance circuit 325 directly commands the robotic arm 130 based on a determined location of the robotic arm via the optical sensors (e.g., LiDAR, sonar, etc.). In other embodiments, the guidance circuit 325 provides information regarding location of the robotic arm 130 to the dispensation circuit 324, and the dispensation circuit 324 provides the commands to the robotic arm 130. For example, as the dispensation circuit 324 is commanding the robotic arm 130 to move, the guidance circuit 325 may determine that the robotic arm 130 is about to hit a shelf based on input from a proximity sensor and provides that information to the dispensation circuit 324 so that the dispensation circuit 324 can command the robotic arm 130 to halt movement. In another example, the guidance circuit 325 utilizes sonar to locate the customer (based on the customer's voice) and provides the customer's location to the dispensation circuit 324 for the dispensation circuit 324 to bring the completed order directly to the customer's location.

The consultation circuit 326 is structured or configured to review details of an active medication order for a customer, evaluate a medical history of the customer, and provide guidance to the customer based on the medication details in light of the customer's medical history. In some embodiments, the consultation circuit 326 first offers guidance to the customer (rather than defaulting to giving guidance) and provides guidance only in response to an affirmative answer from the customer. In response to the affirmative answer, the consultation circuit 326 determines at least one of a name of the medication, a dosage, or a frequency for taking. From there, the consultation circuit 326 either requests medication details from the backend system 340 for the consultation circuit 326 to analyze or sends the determined information to the backend system 340 for the backend system 340 to analyze.

In those embodiments in which the consultation circuit 326 receives the medication details from the backend system 340, the consultation circuit 326 reviews the medication details for any possible issues. For example, if the medication details note that the medication should not be taken with alcohol, the consultation circuit 326 notes that the user should not take the medicine with alcohol. The consultation circuit 326 then requests the customer's medical history from the backend system 340. The medical history here may include details on past medications, past diseases or injuries, current allergies, or current medications. Once the consultation circuit 326 receives the customer's medical history, the consultation circuit 326 compares the medication details to the medical history to identify possible customer-specific issues. This comparison may include a determination if the customer has taken this medication (or any active ingredients in this medication) previously, or if the customer is allergic to any active ingredients in this medication. Further, the comparison may include a determination if the medication interacts with any of the customer's current medication. In those embodiments in which the backend system 340 is performing the analysis, the steps are similar to those described above as performed by the consultation circuit 326 with the addition of the backend system 340 transmitting the results of the analysis to the consultation circuit 326.

The consultation circuit 326 then provides guidance to the customer based on the performed analysis. In some embodiments, the consultation circuit 326 broadcasts the guidance through the speaker 142. Due to the sensitive and protected nature of the guidance (in part because it may be based on the protected information from the second database), the speaker 142 may broadcast at a lower volume, or the consultation circuit 326 may instead display the guidance on a screen (not pictured) or print the guidance on a printer (not pictured). In addition to providing guidance, the consultation circuit 326 may also decline to dispense medication if the analysis shows that the customer would have an adverse reaction to the medication. For example, if the customer's medical history indicates that the customer would have an allergic reaction to the medication, the consultation circuit 326 declines to dispense the medication. The consultation circuit 326 may also decline to dispense the medication if the consultation circuit 326 determines that the medication has expired (e.g., according to the National Drug Code packaging). In some embodiments, if the consultation circuit 326 declines to dispense the medication, the consultation circuit 326 prompts an action and informs the pharmacist at the server side for further action (e.g., provide information to customer regarding allergic reaction).

In some embodiments, the consultation circuit 326 facilitates payment for the medication by the customer. The consultation circuit 326 first determines a price for the medication, which can include querying a market price from a stored spreadsheet or querying an insurance database (provided by one or more insurance companies) for the pricing information associated with a customer's insurance policy. Because the customer's insurance policy information is stored in the backend system 340 and is communicated with the arm computer 310 (and specifically the consultation circuit 326), the consultation circuit 326 may determine and provide a price to the customer without additional input from the customer.

Once the consultation circuit 326 determines the price, the consultation circuit 326 may act as a Point of Sale (POS) device and receive payment directly from the customer. In some embodiments, the pharmacy robot 100 includes a device for receiving a credit card from the customer. In other embodiments, the customer has stored payment information that has been associated with their profile, which the consultation circuit 326 can process with pre-authorization or can ask the customer for authorization to process (e.g., via the speakers 142). Following successful processing of payment, the consultation circuit 326 approves dispensation of the medication.

Figure 6:
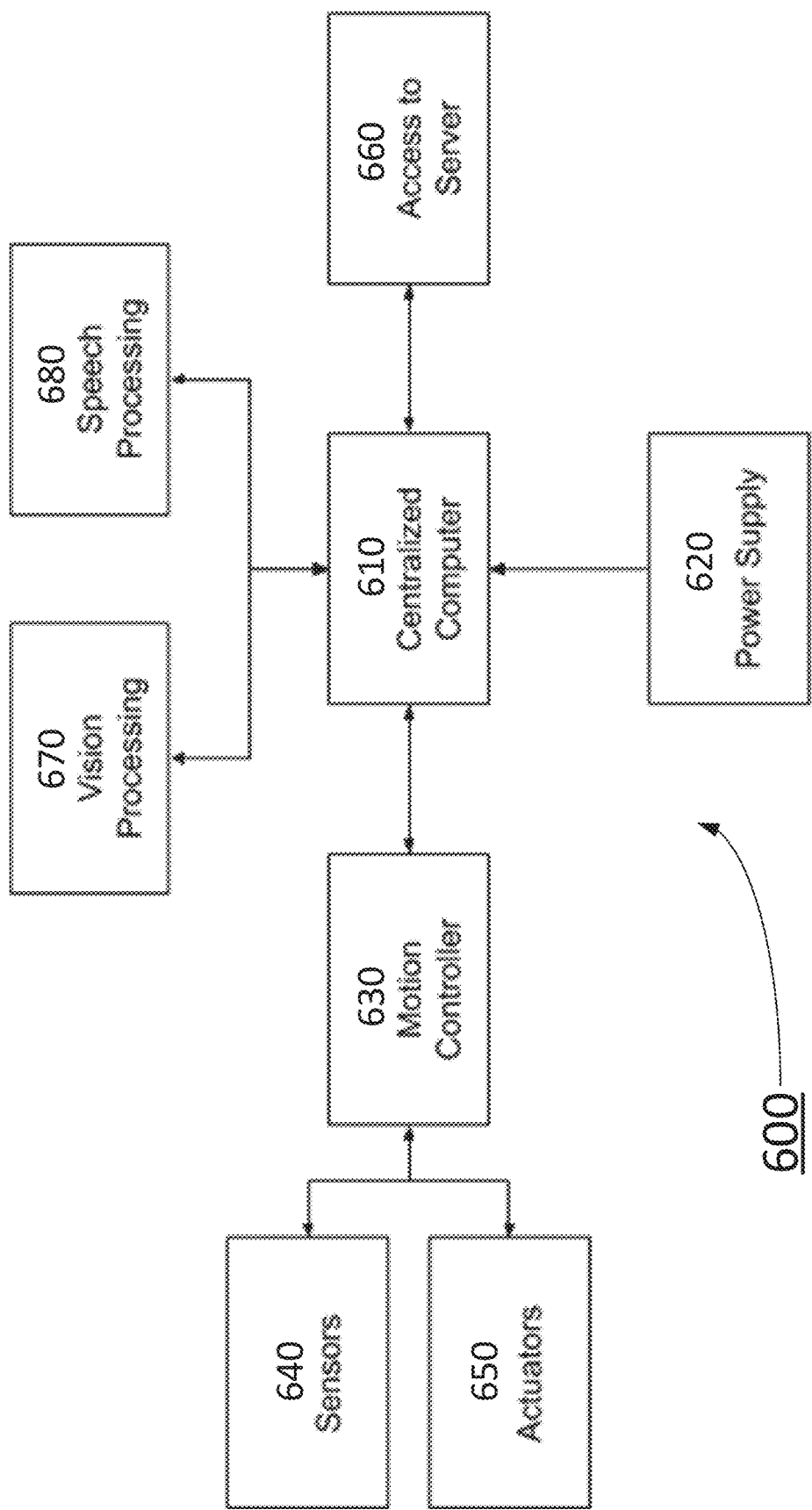
FIG. 6 is a block diagram of a system for operating the pharmacy robot of FIG. 2, according to some arrangements.

FIG. 6 is a block diagram of a computing system 600 for operating the pharmacy robot 100 of FIG. 2, according to some arrangements. As shown in FIG. 6, the computing system 600 includes a centralized computer 610, a power supply 620, a motion controller 630, and a server access 660. The centralized computer 610 is coupled to a vision processing module 670 configured to detect an object's pose or identity and a speech processing module 680 configured to converse with users or customers. The power supply 620 is structured to supply power to the centralized computer 610 and related components. The motion controller 630 may be a motion control module configured to actuate the components of the pharmacy robot 100 (e.g., the robotic arm 130, the first rail 110, the second rail 120, etc.), and may be coupled to one or more sensors 640 and actuators 650. The one or more sensors 640 include cameras, encoders, or electric skin that receive data regarding the pharmacy robot 100. The actuators 650 may include motors or similar components in the robotic arm 130.

Figure 7:
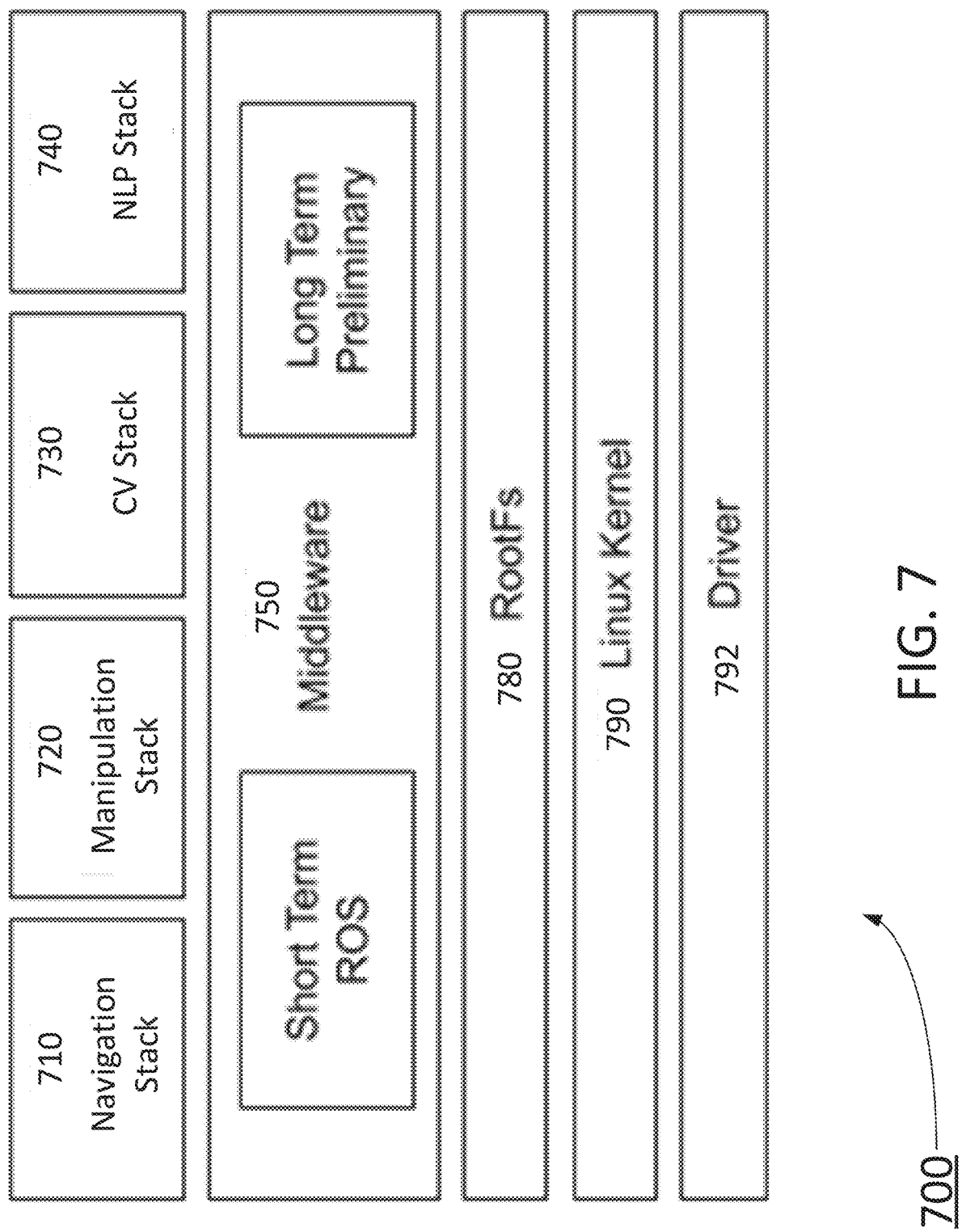
FIG. 7 is a block diagram of a software stack of the system of FIG. 6, according to some arrangements.

FIG. 7 is a block diagram of a software stack 700 of the system of FIG. 6, according to some arrangements. As shown in FIG. 7, the software stack 700 includes a navigation stack 710, a manipulation stack 720, a computer vision (CV) stack 730, and a natural language processing (NLP) stack 740. The navigation stack 710 includes one or more low-level controllers (e.g., proportional-integral-derivative (PID)) for controlling pharmacy robot 100 navigation, and the manipulation stack 720 includes one or more low-level controllers for controlling robotic arm 130 manipulation of objects. The CV stack includes detectors that may be based on an open source library or preliminary software modules (e.g., deep networks, conventional neural networks (CNN), etc.), and the NLP stack 740 includes one or more speech recognition modules and synthesizers that may be based on an open source library or preliminary software modules.

The software stack 700 further includes middleware 750 that distributes computation resources and transmits messages between applications. As shown, the middleware 750 includes short term solutions through robot operating system (ROS) and long term solutions by proprietary software, and may be based on an open source library or proprietary software. From there, the software stack 700 includes root functions (RootFs), which may be open source libraries built upon the Linux system, and Linux Kernel 790, which are Linux kernel software. The software stack 700 includes one or more drivers 792, which include hardware drivers and firmware.

Figure 8:
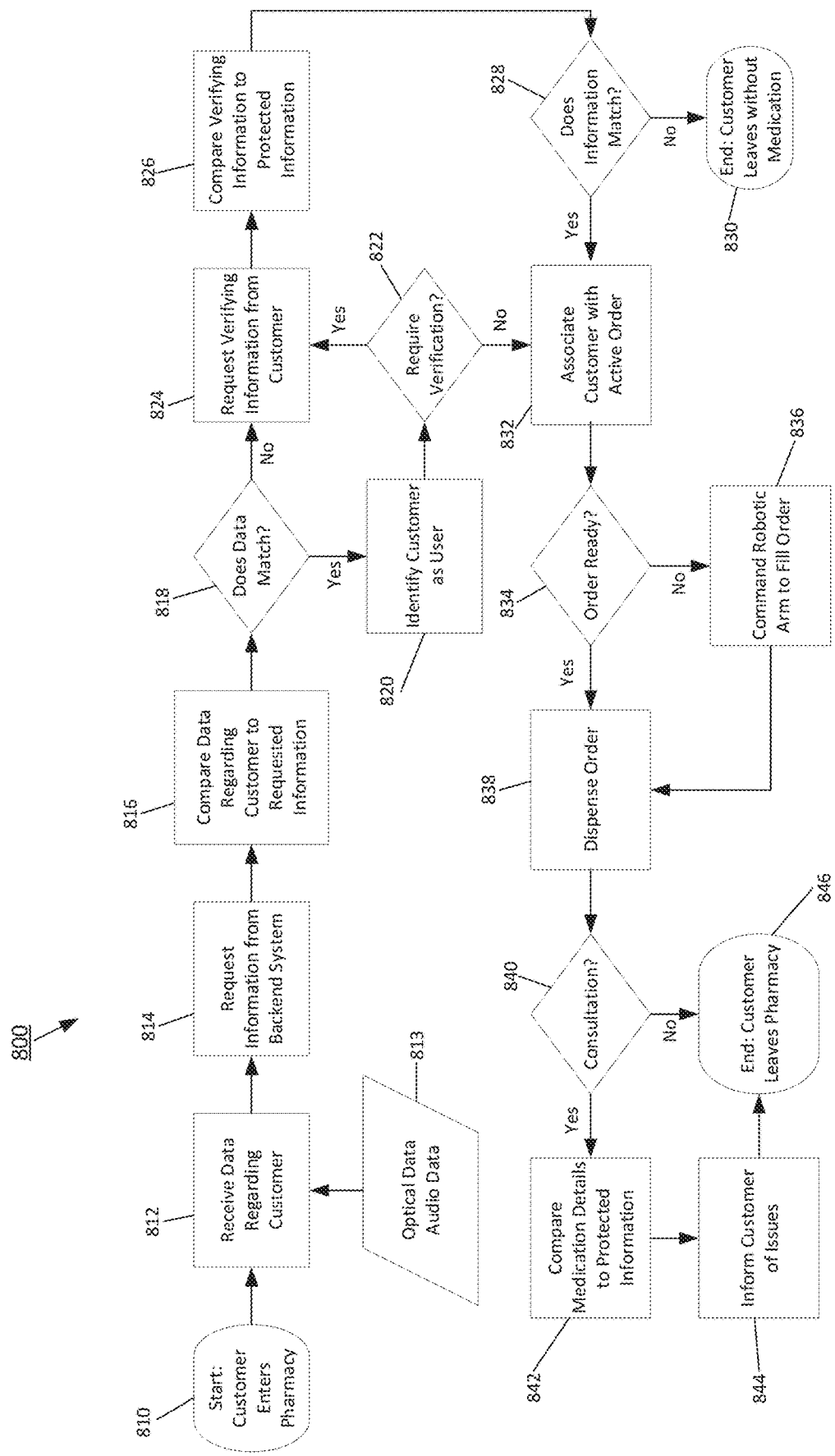
FIG. 8 is a flowchart of a method for servicing a customer at a pharmacy, according to some arrangements.

FIG. 8 is a flowchart for a method 800 for serving a customer at a pharmacy by the pharmacy robot 100. The method 800 begins at 810 when the customer enters the pharmacy. At 812, the pharmacy robot 100 (via the arm computer 310) receives data regarding the entering customer from 813, which includes optical data (from the camera 140) and/or audio data (from the microphone array 144). At 814, the arm computer 310 requests information from the backend system 340 (e.g., information stored in the first database 351), and compares that information to the received customer data at 816. In some embodiments, the arm computer 310 receives information from the backend system 340, and the arm computer 310 performs the identification comparison. In other embodiments, the arm computer 310 sends the data received from the customer to the backend system 340, and the backend system 340 performs the comparison against the requested information. As discussed herein with regard to the identification circuit 320, the requested information may be a pool of information based on one or more active criteria (e.g., active orders). If the customer data matches at least one piece of requested information at 818 (818:YES), the method 800 proceeds to 820 where the customer is identified as a user associated with the matched piece of information. If the customer data does not match any of the requested information (818:NO), the method 800 proceeds to 824 at which the pharmacy robot 100 requests verifying information from the customer.

From 820, the pharmacy robot 100 (e.g., via the arm computer 310) determines if the identified user requires further verification at 822. This determination may be based on pre-programmed criteria, such that every identified customer must also be verified, or may be based on a number of visits, such that an identified customer must be verified for their first visit (i.e., to set up an account). If verification is not required (822:NO), the method 800 proceeds to 832. If verification is required (822:YES), the arm computer 310 proceeds to request verifying information from the customer (e.g., via the speaker 142) at 824. After verifying information is received, the verifying information is compared to protected information that is stored in the backend system 340. As discussed herein with regard to the verification circuit 322, the comparison may be performed by the arm computer 310 (such that the arm computer 310 first receives the protected information from the backend system 340) or by the backend system (such that the arm computer 310 first transmits the protected information to the backend system 340). The protected information may be any type of information that would be known only to authorized individuals and stored in the second database 352. If the verifying information does not match (828:NO), the method 800 ends as the customer is not authorized to pick up medication. If the verifying information does match (828:YES), the method 800 proceeds to 832.

At 832, the arm computer 310 associates the customer with an active order. If the order is ready (834:YES), the pharmacy robot 100 dispenses the order at 838. If the order is not ready (834:NO), the arm computer 310 commands the robotic arm 130 to fill the order. As discussed herein with regard to the dispensation circuit 324, commanding the robotic arm 130 includes issuing commands to individual motors and components of the robotic arm 130 in order to manipulate the robotic arm 130 based on outputs from the camera 140 and one or more sensors (e.g., LiDAR, sonar). Once the order has been filled, the pharmacy robot 100 dispenses the medication at 838.

From there, the pharmacy robot 100 determines if consultation is desired at 840. Consultation may be default or required for all orders, or may be presented as an offer to the customer (e.g., via the speaker 142). If there is no consultation (840:NO), the method 800 ends at 846 when the customer leaves the pharmacy with their order. If consultation is required or requested (840:YES), the method 800 proceeds to 842 where medication details (based on the active order) are compared to protected information. As discussed herein with regard to the consultation circuit 326, the comparison may be performed by the arm computer 310 or the backend system 340. From there, at 844, the arm computer 310 informs the customer of any issues identified as a result of the comparison, after which the customer leaves the pharmacy with their medication at 846.

Figure 9:
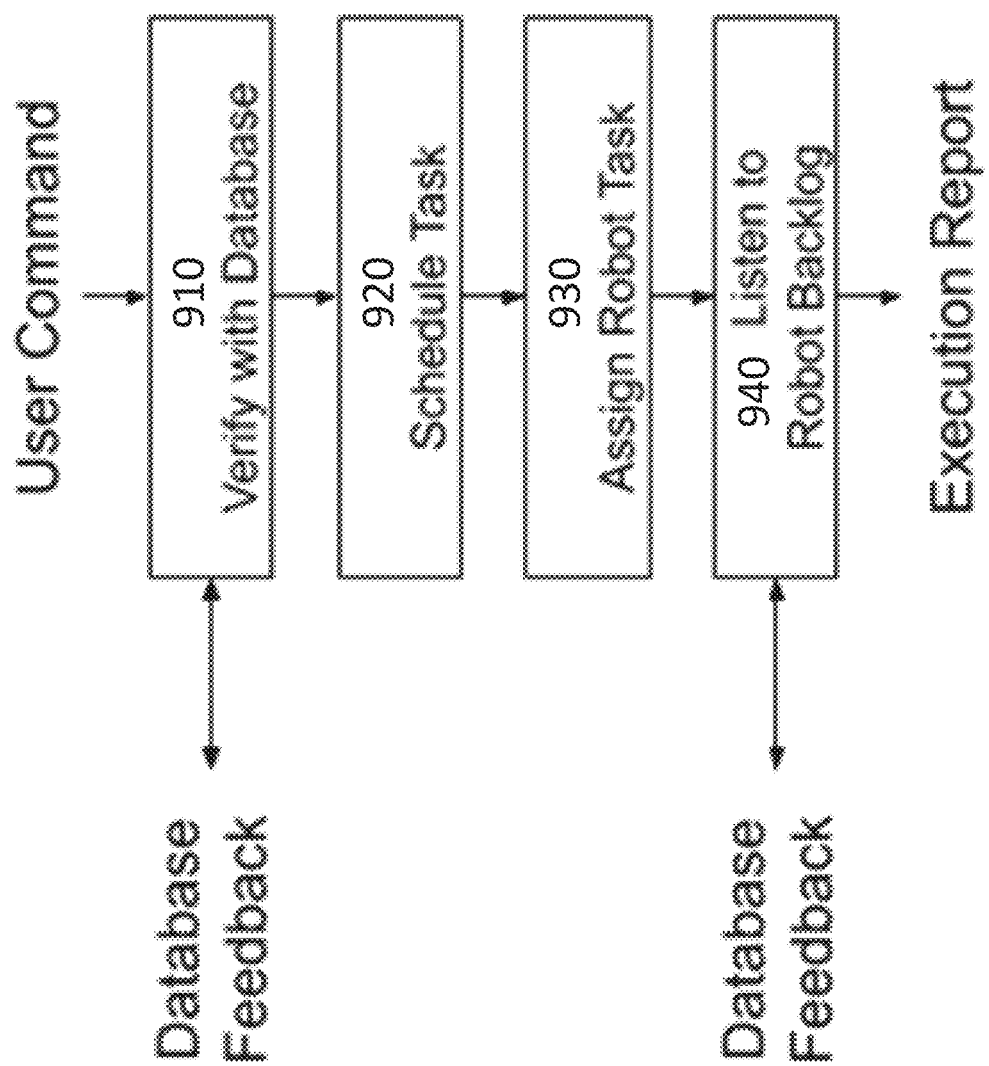
FIG. 9 is a flowchart of a method for commanding the robotic arm of FIG. 3, according to some arrangements.

FIG. 9 is a flowchart of a method 900 for commanding the robotic arm 130 of FIG. 3, according to some arrangements. As shown in FIG. 9, the method 900 is performed by a computing system, such as the server 370, the arm computer 310, and/or the backend system 340, and begins at 910 by verifying a user with a database (e.g., the first database 351, the second database 352). This verification may be performed in response to a user command (e.g., the user asking to be verified) and works based on feedback from the database. From there, the method 900 proceeds to schedule a task for the robotic arm 130 at 920. The task may include any one of dispense medication, locate filled medicine bottle, locate medication to fill medicine bottle, etc., and may be scheduled based on priority, time, and/or frequency. At 930, the task is assigned to the robotic arm 930, and at 940, a backlog of tasks is listened to in order to determine the actions of the robotic arm 130. The backlog of tasks may include a list of tasks previously assigned to the robotic arm 130, which may be ordered based on reception time, priority, or an assigned ranking. Based on the backlog of tasks, an execution report is output, which may be presented to a user and saved in the database.

FIG. 10 is a flowchart of a method 1000 for servicing a customer at a pharmacy, according to some arrangements. As shown in FIG. 10, the method 1000 may be performed by a computing system, such as the arm computer 310. The method 1000 begins at 1010 where the arm computer 310 captures identifying information from a customer. As discussed with regard to the identifying circuit 320, this identifying information may be visual (e.g., a picture or image of the customer), verbal (e.g., a customer's spoken name), or text-based (e.g., a customer's typed name). At 1020, the arm computer 310 identifies the customer based on the identifying information. In some embodiments, the arm computer 310 works with the backend system 340 to perform this identification, and either sends the identifying information to the backend system 340 or receives stored information from the backend system 340. At 1030, the arm computer 310 (working with the backend system 340) associates the customer with a medication order.

Once the arm computer 310 has determined an associated medication order, the arm computer 310 at 1040 commands the robotic arm 130 to move to a container containing medication indicated by the medication order. At 1050, the arm computer 310 commands the robotic arm 130 to retrieve the container by manipulating the jaw 132 around the container. Once the container has been retrieved, the arm computer 310 commands the robotic arm 130 at 1060 to move the container towards the customer.

While in the non-limiting examples show, the joints may be actuated by motors, other suitable mechanisms to actuate movement at the joints may be used, including but not limited to, hydraulics, pneumatic, electric, thermal, magnetic, mechanical, and/or the like. All joints described herein may be controlled by processing circuit 102 to move sequentially or simultaneously.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the examples disclosed herein may be implemented or performed with a general purpose processor, a digital signal processor (DSP), an application specific integrated circuit (ASIC), a field programmable gate array (FPGA), Graphics Processing Unit (GPU), or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In some exemplary examples, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A system for providing medication to a customer, comprising:
    a movable structure, the movable structure comprising:
        a robotic arm comprising one or more joints, one or more actuators, and one or more segments, each of which is structured to move a robotic manipulator coupled to an end of the robotic arm, wherein the robotic manipulator is configured to retrieve and release a container containing the medication;
        a camera; and
        a microphone coupled to the robotic arm; and
    a computing system comprising at least one processor coupled to a memory storing instructions that, when executed by the at least one processor, causes the computing system to perform operations comprising:
    capturing identifying data regarding a customer via the microphone, wherein the identifying data comprises audio data;
    identifying the customer based on at least the audio data of the identifying data;
    associating the customer with a medication order; and
    retrieving the medication from the medication order by:
        moving the robotic arm adjacent to the container containing the medication based on predetermined mapping, the predetermined mapping comprising logged locations of filled orders, the logged locations comprising a location of the container containing the medication;
        retrieving the container using the robotic manipulator based on at least one image or at least one video captured by the camera; and
        moving the container toward the customer by moving the robotic arm.

2. The system of claim 1, wherein the identifying data is further captured by the camera.

3. The system of claim 1, wherein identifying the customer based on the identifying data further comprises:
    requesting, from a backend system, information regarding one or more users;
    comparing the identifying data to the requested information; and
    in response to the identifying data matching information associated with a user of the one or more users, identifying the customer as the user.

4. The system of claim 1, wherein the operations further comprise:
    prior to retrieving the medication, verifying that the customer is authorized to pick up the medication.

5. The system of claim 4, wherein verifying that the customer is authorized comprises:
    requesting verifying information from the customer;
    comparing the verifying information to protected information associated with a user in a backend system; and
    in response to the verifying information matching the protected information, determining that the customer is authorized.

6. The system of claim 5, wherein the protected information comprises at least one of a medical history of the customer, a current medication of the customer, or a current allergy of the customer.

7. The system of claim 1, wherein associating the customer with the medication order further comprises:
identifying the medication order based on the customer;
determining whether the medication order is ready; and
in response to the medication order not being ready, commanding the robotic arm to perform operations to complete the medication order.

8. The system of claim 1, wherein the operations further comprise:
determining medication details associated with the medication;
comparing the medication details to at least one of a medical history of the customer, a current medication of the customer, or a current allergy of the customer;
determining one or more issues based on the comparison; and
informing the customer of the one or more issues.

9. The system of claim 8, wherein determining one or more issues comprises at least one of:
determining that the medication is expired;
determining that the customer has previously had an adverse reaction to the medication or an active ingredient of the medication based on the medical history;
determining that the medication or the active ingredient of the medication would have an adverse reaction with the current medication; or
determining that the current allergy comprises the medication or the active ingredient of the medication.

10. The system of claim 8, wherein informing the customer comprises broadcasting the one or more issues via a speaker coupled to the robotic arm.

11. The system of claim 1, further comprising a backend system communicatively coupled to the computing system and structured to store information associated with one or more users in a database.

12. The system of claim 11, wherein the database comprises a first database and a second database, the first database storing identifying information associated with the one or more users and the second database storing verifying information associated with the one or more users.

13. The system of claim 11, wherein the backend system is a cloud-based computing system.

14. The system of claim 11, wherein the backend system is further configured to compile profiles of customer data from the information stored in the database.

15. A method for providing medication to a customer, comprising:
capturing identifying data regarding a customer via a microphone coupled to a robotic arm, wherein the identifying data comprises audio data;
identifying the customer based on at least the audio data of the identifying data;
associating the customer with a medication order; and
retrieving the medication from the medication order by:
moving the robotic arm adjacent to a container containing the medication based on predetermined mapping, the predetermined mapping comprising logged locations of filled orders, the logged locations comprising a location of the container containing the medication;
retrieving the container using a robotic manipulator of the robotic arm based on at least one image or at least one video captured by a camera of the robotic arm; and
moving the container toward the customer by moving the robotic arm.

16. The method of claim 15, wherein identifying the customer based on the identifying data further comprises:
requesting, from a backend system, information regarding one or more users;
comparing the identifying data to the requested information; and
in response to the identifying data matching information associated with a user of the one or more users, identifying the customer as the user.

17. The method of claim 15, further comprising prior to retrieving the medication, verifying that the customer is authorized to pick up the medication,
wherein verifying that the customer is authorized comprises:
requesting verifying information from the customer;
comparing the verifying information to protected information associated with a user in a backend system; and
in response to the verifying information matching the protected information, determining that the customer is authorized.

18. The method of claim 15, further comprising:
determining medication details associated with the medication;
comparing the medication details to at least one of a medical history of the customer, a current medication of the customer, or a current allergy of the customer;
determining one or more issues based on the comparison; and
informing the customer of the one or more issues.

19. The method of claim 18, wherein informing the customer comprises broadcasting the one or more issues via a speaker coupled to the robotic arm.

20. The method of claim 15, further comprising communicating with a cloud-based computing system structured to store information associated with one or more users in a database.

\* \* \* \* \*